United States Patent [19]

Guibet et al.

[11] 4,398,920

[45] Aug. 16, 1983

[54] BLENDED FUELS CONTAINING BUTYL ALCOHOL ACETONE AND METHANOL

[75] Inventors: Jean-Claude Guibet, Saint Germain en Laye; Jean-Paul Vandecasteele, Fourqueux, both of France

[73] Assignee: Institut Francais du Petrole, Rueil-Malmaison, France

[21] Appl. No.: 271,758

[22] Filed: Jun. 9, 1981

[30] Foreign Application Priority Data

Jun. 9, 1980 [FR] France ............................. 80 12822
Aug. 1, 1980 [FR] France ............................. 80 17147

[51] Int. Cl.$^3$ ............................................. C10L 1/18
[52] U.S. Cl. ...................................... 44/56; 44/77
[58] Field of Search ........................... 44/56, 53, 77

[56] References Cited

U.S. PATENT DOCUMENTS 1,570,060  1/1926  Hammond ........................ 44/56
2,088,000  7/1937  Savage ............................. 44/56
4,300,912 11/1981  Townsend ........................ 44/56

FOREIGN PATENT DOCUMENTS 814205 11/1936 France .
187335 10/1922 United Kingdom .
409730  5/1934 United Kingdom .
415312  8/1934 United Kingdom .
458922 12/1936 United Kingdom .
464755  4/1937 United Kingdom .

Primary Examiner—Jacqueline V. Howard
Attorney, Agent, or Firm—Millen & White

[57] ABSTRACT

A blended fuel comprising
(a) a gasoline, a gas oil or a fuel oil;
(b) a mixture of butanol and acetone, optionally also containing isopropanol and/or ethanol; and
(c) methanol; the mixture (b) being producible by fermentation of a hydrolysate obtained by hydrolyzing a cellulosic substrate by means of cellulolytic enzymes prepared by fermentation of a suitable organism such as bacteria of the Clostridium genus or fungi of the Sporotrichum, Polyporus, Penicillium, Fusarium, Myrothecium or Trichoderma genera.

16 Claims, No Drawings

BLENDED FUELS CONTAINING BUTYL ALCOHOL ACETONE AND METHANOL

This invention concerns new motor fuels and new fuels which can be used, for example, as gasolines for motor cars or as motor fuels for Diesel engines. These motor fuels have octane and cetane numbers generally higher than those of conventional gasolines or gas oils and may be used without decrease of the compression ratio of the engines. The motor fuels or fuels according to the invention contain:
- (a) a conventional motor fuel or fuel i.e. a conventional motor fuel or fuel selected from the group consisting of hydrocarbon gasoline (for cars), gas-oil and domestic fuel oil (heating oil),
- (b) a mixture of butanol (n-butanol) with acetone and
- (c) methanol.

By way of example of hydrocarbon gasoline which can be used in the motor fuel or fuel composition according to the invention, there can be mentioned, for example, gasoline issued from a reforming unit and/or a catalytic or non-catalytic cracking unit.

The motor fuels or fuels according to the invention may have other utilizations than as gasoline for cars or motor fuels for Diesel engines. Thus they can be used as motor fuels in motors used in agricultural sectors (tractor engines for example) or otherwise as fuels in various heating plants.

The motor fuels or fuels according to the invention contain by weight:
- (a) from 5 to 97% or preferably from 65 to 93% or more preferably from 75 to 90% of gasoline or gas-oil or fuel oil (or still, in accordance with specific utilisations, 35 to 85% or 45 to 80%);
- (b) 95 to 1% or 95 to 5%, preferably 35 to 7% or more preferably 25 to 10% of a mixture of butanol with acetone; according to the specific utilisations concerned, there can also be used from 15 to 65% or from 20 to 55% of said mixture, or still from 1 to 10% thereof. The mixture contains, by weight, from 40 to 85% of butanol and from 15 to 60% of acetone; and
- (c) 1 to 25% and preferably from 3 to 15% or, more preferably, 7 to 12% of methanol.

An excellent motor fuel according to the invention may contain by weight, for example:
- (a) from 80 to 96% of a conventional fuel or motor fuel,
- (b) from 1 to 10% of said butanol-acetone mixture, and
- (c) from 3 to 10% of methanol.

As preferred example, there can be mentioned a motor fuel containing about 94% of gasoline for cars, 2% of a 60–40% mixture of butanol and acetone and 4% of methanol.

According to the invention, this mixture may also contain, in addition to n-butanol and acetone, either isopropanol or ethanol or both isopropanol and ethanol.

When this mixture contains isopropanol, it preferably further contains, by weight, from 50 to 85% of butanol, 15 to 25% of acetone and 5 to 35% of isopropanol.

As above-mentioned, in some cases, it may be convenient to add ethanol to said mixture (containing butyl alcohol and acetone) in the following proportions by weight: 40 to 80% of butanol, 15 to 45% of acetone and 1 to 15% of ethanol. A motor fuel according to the invention which is particularly convenient contains:
- (a) 94% of gasoline for cars,
- (b) 2% of a 65-30-5 or 60-30-10 mixture of butanol, acetone and ethanol respectively and
- (c) 4% of methanol.

As above-mentioned, specific mixtures can be used, which contain simultaneously butyl alcohol, acetone, isopropanol and ethanol in the following proportions by weight:

45 to 75% of butanol, 15 to 25% of acetone, 10 to 30% of isopropanol and 1 to 10% of ethanol (preferably 4 to 9%).

By way of example, it is contemplated to admix gasoline for cars (premium gasoline) with each of the two mixtures A or B as hereinafter defined. The effect of methanol will be indicated later on. A first mixture, which is called A, contains by weight 75% of butyl alcohol and 25% of acetone.

This mixture has an octane number RON of 99.5 and a MON number of 86.4. A second mixture, which is called B, contains by weight 70% of butyl alcohol, 15% of acetone and 15% of isopropanol and has a RON of 101.2 and a MON of 87.0. (RON=Research octane number; MON=Motor octane number).

Thus the combination of such mixtures as A and B with another gasoline having an octane number lower than that of these mixtures, has the effect of unexpectedly increasing the octane number of said gasoline, particularly when adding amounts, even small, of methanol, for example 1 to 10% by weight of methanol with respect to the total mixture.

The fuels or motor fuels according to the invention have boiling temperatures of the same order as those of the conventionally used gasoline components or motor fuels. Their supply to an engine and carburation are effected easily.

The fact that the fuels or motor fuels according to the invention contain several compounds of different boiling points which are regularly distributed, provides for a continuous distillation curve as in the case of motor fuels of the trade.

Certain types of mixtures may be preferred, depending on the conditions of use. For example, a motor fuel containing a mixture such as above defined, is more particularly recommended in winter in view of its high acetone content which provides for a better behaviour when starting the engine and running with this motor fuel. Conversely, a motor fuel containing a mixture such as B, as above defined, is more appropriate for a motor fuel of the "summer type".

In admixture with conventional gasolines, mixtures such as A and B are perfectly compatible with the other components of conventional gasolines and do not produce any distortion in the distillation cruve, in contrast with what is observed with motor fuels containing gasoline and at least one light alcohol, particularly methanol. When testing the behaviour of a motor fuel for preparing a gasoline composition, the percents of the mixture distilling respectively at 70° C. and 100° C. are often considered as representative values. It is observed that a proportion of the products A and B, for example, 25 to 50% (by weight), can be added to conventional gasoline for cars without substantially modifying the percents distilled at 70° C. and 100° C., as can be observed from the following Table I:

TABLE I

|  | % DISTILLED at 70° C. | % DISTILLED at 100° C. |
| --- | --- | --- |
| Conventional gasoline | 25.5 | 52 |
| Conventional gasoline + 25% of A | 25 | 51 |
| Conventional gasoline + 50% of A | 22 | 46 |
| Conventional gasoline + 25% of B | 25.5 | 53 |
| Conventional gasoline + 50% of B | 20 | 47 |

Conventional gasoline is intended to mean premium gasoline for cars having the specifications required during year 1980, i.e., a RON from 97 to 99 and a regular distillation curve, with an initial boiling point from 28° to 35° C. and a final boiling point from about 180° to 200° C.

On the other hand, it is known that methanol cannot be added directly to gasoline, fuel or gas-oil in view of the spontaneous demixion phenomenon, which is enhanced by the presence of even a small amount of water. It has now been observed that mixtures such as A and B, and, more generally, butanol-acetone mixtures optionally containing isopropanol and/or ethanol in the above-mentioned proportions, are compatible with the addition of up to 25% and preferably up to 12% by weight of methanol, without decrease of the performance of these fuels or motor fuels. The addition of ethanol, for example, to a fuel or motor fuel containing gasoline for cars, methanol and a mixture of butanol and acetone, increases the water compatibility of the fuel or motor fuel. The motor fuels obtained by admixing conventional gasoline with mixtures such as A and B, thus keep the characteristics indicated in Table I, after addition of at most 25% by weight of methanol with respect to the total motor fuel.

The fuels or motor fuels according to the invention also have good thermal properties. Thus, for example, the above-described mixtures A and B have a calorific power of about 7650 Kcal/kg, or 31977 Kjoules/kg, i.e. a better calorific power than that of the motor fuels containing exclusively alcohols and particularly methanol (4764 Kcal/kg, i.e. 19900 Kjoules/kg). In the case of mixtures A and B, the weight ratio air/motor fuel corresponding to the stoichiometrical adjustment is about 10.8 instead of 14.4 in the case of a conventional motor fuel and 6.4 in the case of methanol. The modifications of the adjustment effected in order to adapt the engines to the operation with the fuels or motor fuels according to the invention, are thus less important than the modifications which would have been required if these motors were operated with methanol alone instead of conventional gasoline. When the fuel or motor fuel contains small amounts of such a mixture as A or B, for example less than 10% by weight and from about 1 or 2 to 8% of methanol (by weight), the required modifications are substantially insignificant and accordingly, need not be effected.

The vaporization heat of the motor fuels A and B is about 140 cal/g, i.e. 585 joules/g, accordingly relatively close to that of conventional motor fuels (70 to 80 cal/g, i.e. 290 to 335 joules/g). On the contrary, in a motor fuel consisting of methanol, the vaporization heat is very high (262 cal/g, i.e. 1095 joules/g) and the carburation thus requires a substantial supply of external heat. For example, in order to obtain one liter of carburated mixture with a richness of 1, it is required, at 25° C. under 1 atmosphere (0.1 MPa):

188 joules (44.9 cal) in the case of methanol 25.9 joules (6.2 cal) in the case of a conventional motor fuel 56 to 57 joules (about 13.4 to 13.7 cal) in the case of such mixtures as those of type A or B.

The high octane number (RON close to 110) of acetone, which is the most volatile constituent of the described mixtures, imparts to these motor fuels a low $\Delta R$ (the $\Delta R$ gives indications on the octane equilibrium along the distillation curve), this being highly satisfactory in order to improve the behaviour of the engine during acceleration starting from low running speeds.

These motor fuels when added to constituents with a high $\Delta R$ (for example catalytic reforming effluents, gasolines containing high proportions of these effluents), make it possible to obtain a satisfactory $\Delta R$.

In a specific example, there was obtained a very satisfactory $\Delta R$ of 7.5 by adding 25% by weight of mixture A and 5% of methanol to a gasoline having a high initial $\Delta R$ of the order of 12.5.

It is observed that, according to this invention, methanol addition to a gasoline containing a butanol-acetone mixture increases the octane numbers of such a mixture with a synergistic effect and that, simultaneously, the presence of the butanol-acetone mixture makes it, possible to substantially decrease the undesirable effects of methanol, particularly the demixion phenomenon. The overall effect is as if methanol on the one hand, and the butanol-acetone mixture on the other hand, enhanced their respective effects.

Another advantage of the fuels or motor fuels according to the invention, such as the above-defined motor fuels A and B, in admixture with a conventional gasoline and with methanol lies, as above-indicated, in the fact that they are not liable to demixion in the presence of water, as is the case, for example, of a motor fuel with a high methanol concentration. It results therefrom that the fuels or motor fuels according to the invention are compatible with the presence of water i amounts which may reach, for example, depending on the composition of the mixtures used, up to 100 g of water or more per liter of mixture at 0° C.

The butanol-acetone mixtures optionally containing isopropanol and/or ethanol, are prepared according to any convenient method, for example by mere/mixing of the constituents thereof. But it has also been discovered that a particularly advantageous method for obtaining them consists of: (a) preparing cellulolytic enzymes by fermentation of a convenient organism, (b) subsequently hydrolyzing at least one cellulosic substrate by means of the cellulolytic enzymes prepared in step (a) so as to obtain a hydrolysate and (c) proceeding to the fermentation of said hydrolysate.

The convenient organism used in step (a) for the production of cellulolytic enzymes is generally a fungus belonging preferably to the Sporotrichum, Polyporus, Fusarium, Penicillium, Myrothecium and Trichoderma Species or a bacterium belonging preferably to the Clostridium genus.

The cellulosic substrates used in step (b) are, for example, those obtained after pretreatment of waste papers, corn straw, bagasse, corn cobs and stalks, leafy and resinous wood waste from sawmills or forest. These pretreatments may be mechanical (crushing, for example) and/or chemical (for example, treatment with sodium hydroxide, preferably with about 6% of sodium hydroxide weight/substrates weight). The hydrolysis to sugars (enzymatic reaction) forming step (b) is then conducted according to usual means, preferably at a temperature from 30° to 60° C., at a pH generally from 3.5 to 6.5, these operating conditions depending essentially on the nature of the enzymatic system.

The fermentation which is conducted in step (c) is performed on the hydrolysates obtained in step (b) to which are added nutrients. These organisms are bacteria, belonging preferably to the Clostridium genus. The fermentation is of the anaerobic type and is generally conducted at a temperature from 25° to 40° C. and at a pH generally from 4 to 7.5.

Factors having an effect on the composition of the obtained mixtures are the strain, the substrate and the fermentation conditions, i.e. pH, temperature, composition of the medium and particularly the nitrogen source.

More precisely, the organisms used for the acetone/-butanol fermentation are bacteria, generally pertaining to the Clostridium genus. The described species are referred to as *Clostridium saccharoacetobutylicum, Clostridium acetobutylicum, Clostridium saccharobutylacetonicum, Clostridium saccharoperbutylicum*. A typical species is *Clostridium acetobutylicum*.

The organisms used for the butanol/isopropanol fermentation, which are close to the preceding ones, also pertain to the Clostridium genus. The species are those described as *Clostridium propylbutylicum, Clostridium viscifasciens*, but the preferred types of species according to this invention are *Clostridium butylicum, Clostridium beijerinckii* and *Clostridium toanum*.

The operating conditions provide for:
(a) by acetone/butanol fermentation, a mixture whose composition by weight is, for example, as follows:
n-butanol: 40–80%
acetone: 15–45%
ethanol: 0–15%
(b) by butanol/isopropanol fermentation, a motor fuel having, for example, the following composition by weight:
n-butanol: 45–75%
acetone: 2–15%
ethanol: 0–10%
isopropanol: 10–30%

It must be observed that the butanol/acetone or butanol/isopropanol fermentation is possible in another original manner, consisting of making use, instead of cellulosic substrates, of Jerusalem artichokes which, after washing, extraction and pressing, are subjected to hydrolysis in order to proceed subsequently to a fermentation of the obtained hydrolysate.

EXAMPLE 1

There is made a mixture containing 25% by weight of motor fuel A, as defined hereinabove with 75% by weight of gasoline issued from a catalytic cracking unit and having a RON (Research octane number) of 85 and a MON (Motor octane number) of 80.

Another mixture is formed, containing 50% by weight of motor fuel A with the same gasoline as above.

There are then formed two other mixtures with the same gasoline as above-mentioned, the first of these mixtures containing 25% by weight of motor fuel B, as defined hereinabove, the second of these mixtures containing 50% by weight of the same motor fuel B.

The mixture numbers of these motor fuels A and B in the four resulting mixtures are given in Table II. The numbers are higher when adding methanol to the four tested mixtures: as a matter of fact, it has been observed that the methanol addition results in a 0.3 point to 0.4 point increase of the octane number RON or MON for each methanol percent added (by weight with respect to the fuel or motor fuel). Thus, when adding 5% by weight of methanol, the RON and MON numbers of the first mixture of Table II take respectively the values of 101.8 and 88.3 and the RON and MON numbers of the third mixture of Table II take respectively the values of 105.9 and 90.

TABLE II

| OBTAINED FUEL or MOTOR FUEL (% b. w.) | RON | MON |
|---|---|---|
| | OCTANE NUMBER OF THE MIXTURE | |
| 25% of mixture A | A: 100.0 | A: 86.5 |
| 50% of mixture A | A: 100.8 | A: 87.2 |
| 25% of mixture B | B: 104.0 | B: 88.1 |
| 50% of mixture B | B: 104.0 | B: 88.2 |
| Comparatively: | OCTANE NUMBERS | |
| mixture A alone | 99.5 | 86.4 |
| mixture B alone | 101.2 | 87.0 |

EXAMPLE 2

Table III shows the water amount acceptable in the motor fuels or motor fuel mixtures according to the invention.

It is observed that, in the tested motor fuels, the best tolerances to water are obtained with fuels or motor fuels conforming with the invention, containing relatively substantial amounts of butanol-acetone mixture (for example 50%). In fact, in practice, the precisely selected fuels or motor fuels contain substantially less of the butanol-acetone mixture and accordingly, have tolerances to water which are not so good but have the advantage of being used without modification or even without adjustment of the engines which may thus be fed with fuels or motor fuels presently available in the trade (normal gasoline, premium gasoline, gas-oil, fuel oil, etc . . . ) and with the fuels or motor fuels conforming with the invention. Briefly stated, attention must be paid to the fact that the commercial conditions often make it necessary to use fuels or motor fuels whose compositions are not obligatorily those corresponding to the compositions giving the best results. This is the reason for the relatively wide range of the concentration values for the various constituents given by way of preferred examples in this patent application.

TABLE III

| MOTOR FUEL COMPOSITION (% by weight) (conventional premium gasoline containing 65% by weight of aromatics) | | TOLERABLE WATER AMOUNT (Acceptable water amount at 0° C. in g/l) |
|---|---|---|
| Conventional premium gasoline | 92% | 0.50 |
| Methanol | 8% | |
| Conventional premium gasoline | 85% | 1.00 |
| Methanol | 15% | |
| Conventional premium gasoline | 87% | 3.25 |
| Methanol | 8% | |
| A | 5% | |
| Conventional premium gasoline | 75% | 9 |
| Methanol | 15% | |
| A | 10% | |
| Conventional premium gasoline | 67% | 22 |
| Methanol | 13% | |
| A | 20% | |
| Conventional premium gasoline | 50 | 60.5 |
| Mixture | 50 | |
| 59% butanol | | |
| 8% ethanol | | |
| 6% acetone | | |
| 27% isopropanol | | |

TABLE III-continued

| MOTOR FUEL COMPOSITION<br>(% by weight)<br>(conventional premium gasoline containing 65% by weight of aromatics) | | TOLERABLE<br>WATER AMOUNT<br>(Acceptable water<br>amount at 0° C. in g/l) |
|---|---|---|
| Conventional premium gasoline | 50 | 52.5 |
| Mixture | 50 | |
| 66% butanol | | |
| 29% acetone | | |
| 5% ethanol | | |
| Conventional premium gasoline | 50 | 59.8 |
| Mixture | 45 | |
| 59% butanol | | |
| 8% ethanol | | |
| 6% acetone | | |
| 27% isopropanol | | |
| Methanol | 5 | |
| Conventional premium gasoline | 50 | 51.9 |
| Mixture | 50 | |
| 66% butanol | | |
| 29% acetone | | |
| 5% ethanol | | |
| Methanol | 5 | |

EXAMPLE 3

A 10% suspension by weight of crushed newspapers is hydrolyzed to sugars by making use as cellulases of a culture filtrate of fungus *Trichoderma viride* QM 9414, in an amount of 10 international units per gram of substrate. After 48 hours, there is thus obtained at 50° C. and at a pH of 4.8, reducing sugars in an amount of 38 g of which 29 g are glucose.

From a 10% suspension of straw treated with sodium hydroxide, there is obtained, under the same conditions, 46 g of reducing sugars containing 20.5 g of glucose and 15 g of aldopentoses.

An acetonobutylic fermentation is conducted on a portion of these hydrolysates, with nutrient added thereto, according to known techniques at 30° C. and an initial pH of 6, in the presence of the bacteria *Clostridium acetobutylicum*. From the hydrolysate of newspaper there is obtained, after 70 hours, with a yield by weight of 28.5%, a mixture C containing, by weight, 66% of butanol, 29% of acetone and 5% of ethanol. From the straw hydrolysate, there is obtained, after 70 hours, with a yield by weight of 27%, a mixture D containing, by weight, 73% of butanol, 25% of acetone and 2% of ethanol.

EXAMPLE 4

A butanol/isopropanol fermentation is conducted on another portion of the hydrolysates prepared in example 3, according to conventional techniques, in the presence of the bacteria *Clostridium butylicum*. The operation is conducted at 37° C. and at an initial pH of 6.5. An incubation time of 100 hours is used and there is obtained, from the hydrolysate of the newspapers, with a yield by weight of 26.5%, a mixture E containing, by weight, 65% of n-butanol, 5% of ethanol, 16% of isopropanol and 14% of acetone, while, from the straw hydrolysate, there is obtained, with a yield by weight of 31%, a mixture F containing, by weight, 59% of n-butanol, 8% of ethanol, 6% of acetone and 27% of isopropanol.

The following Table IV indicates that RON and MON octane numbers of the mixtures obtained in examples 3 and 4.

TABLE IV

| | RON | MON |
|---|---|---|
| C | 100.5 | 87.2 |
| D | 99.9 | 86.6 |
| E | 102.1 | 87.6 |
| F | 103.5 | 88.3 |

The so-prepared mixtures C, D, E and F are perfectly convenient for being admixed (a) with a conventional gasoline or a fuel or a gasoil and (b) with methanol in the above-mentioned proportions so as to provide an excellent fuel or motor fuel. It must be recalled that for each methanol percent, the RON and MON octane numbers are increased by 0.3 to 0.4 point.

EXAMPLE 5

There is taken again the mixture which contains 75% of butyl alcohol and 25% of acetone by weight. It is admixed with ordinary gas-oil as available in the trade (whose characteristics are given in Table V) in the following proportions by weight: 80% of gas-oil, 20% of mixture A (i.e. finally: gas-oil 80%, butanol 15%, acetone 5%).

The so-obtained characteristics of the mixture with gas-oil of mixture A are compared in Table V. Slightly better characteristics are obtained by adding 5% of methanol by weight with respect to the total mixture. No demixion occurs.

TABLE V

| | | GAS-OIL<br>of the TRADE | 80% gas-oil +<br>20% mixture A<br>(weight) |
|---|---|---|---|
| Volumic mass at 20° C. (g/ml) | | 0.8275 | 0.821 |
| P.C.I. (Kjoules/kg)<br>(heating power) | | 42419 | 40369 |
| Viscosity at 20° C. | | 4.16 centistokes<br>i.e. 4.16 × 10$^{-6}$<br>m$^2$/sec. | 2.91 |
| Cetane number | | 54 | 41 |
| Flash point | (°C.) | 78 | <10 |
| Cloud point | (°C.) | −2 to −3 | −1 to −2 |
| Pour point | (°C.) | −15 to −18 | −15 to −18 |
| Filter-plugging-<br>temperature-limit | (°C.) | −7 to −8 | −4 to −5 |

The gas-oil of the trade, as used above, contains an additive imparting thereto good characteristics in the cold (winter gas-oil).

EXAMPLE 6

Example 5 is repeated by making use successively of 2 gas-oils slightly different from that used in example 5, i.e. a gas-oil without additive and a gas-oil of the "summer type". The results obtained are respectively indicated in Tables VI and VII.

TABLE VI

| | | GAS-OIL OF<br>THE TRADE<br>without additive | 80% GAS-OIL +<br>20% MIXTURE A |
|---|---|---|---|
| Cloud point | (°C.) | +7 | +9 |
| Pour point | (°C.) | −3 | −6 |
| Filter-plugging-<br>temperature-limit | (°C.) | +7 | +6 |

TABLE VII

|  |  | GAS-OIL OF THE TRADE (Summer type) | 80% GAS-OIL + 20% MIXTURE A |
|---|---|---|---|
| Cloud point | (°C.) | +3 | +1 |
| Pour point | (°C.) | −12 | −15 |
| Filter-plugging-temperature-limit | (°C.) | −1 | −5 |

From Tables V to VII, it is apparent that the addition of a butanoacetone mixture to gas-oil provides a very suitable motor fuel whose characteristics, if not sufficient, may still be easily improved by addition of appropriate additives. The advantage of the so-obtained motor fuel is that methanol can be added thereto without producing demixion.

EXAMPLE 7

A motor test has been conducted in order to appreciate the possibility of use of a motor fuel containing a mixture of 80% of gas oil of example 5 with 20% of mixture A.

The selected engine was a traction engine, with a prechamber of the Ricardo type, with a standard adjustment for ordinary gas-oil.

Despite the different properties of the additive containing gas-oil, no modification has been brought to the adjustment of the engine for the test and, consequently, no new optimisation has been searched for at this stage as far as the emissions and yields are concerned.

In these conditions, the results obtained for two typical running speeds of the engine (running speed with maximum torque: 2000 r/min and maximum running speed of the engine: 4150 r/min) are indicated in Tables VIII and IX.

TABLE VIII

| (running speed with maximum torque: 2000 r/min) | | | | |
|---|---|---|---|---|
| Horse power (DIN) | 12.8 | 26.0 | 39.0 | 48.4 |
| Specific consumption with gas-oil alone (kcal/Hp.h) | 2404 | 1993 | 1887 | 1955 |
| Specific consumption with gas-oil + mixture A (80%–20%) (kcal/Hp.h) | 2334 | 1900 | 1823 | 1871 |
| Exhaust temperature with gas-oil alone (°C.) | 245 | 382 | 475 | 575 |
| Exhaust temperature with gas-oil + mixture A (80%–20%) (°C.) | 210 | 320 | 450 | 550 |
| Smokes with gas-oil (Bosch index) | 0.7 | 1.6 | 1.5 | 2.2 |
| Smokes with gas-oil alone + mixture A (80%–20%) (Bosch index) | 0.6 | 0.7 | 1.2 | 2.1 |

TABLE IX

| (maximum running speed of the engine: 4150 r/min) | | | | |
|---|---|---|---|---|
| Horse power (DIN) | 18.3 | 36.5 | 54.8 | 73.0 |
| Specific consumption with gas-oil alone (kcal/Hp.h) | 4358 | 2929 | 2503 | 2443 |
| Specific consumption with gas-oil + mixture A (80%–20%) (kcal/Hp.h) | 4408 | 2971 | 2440 | 2411 |
| Exhaust temperature with gas-oil alone (°C.) | 360 | 440 | 540 | 685 |
| Exhaust temperature with gas-oil + mixture A (80%–20%) (°C.) | 365 | 445 | 540 | 685 |
| Smokes with gas-oil (Bosch index) | 0.8 | 1.3 | 1.1 | 0.9 |
| Smokes with gas-oil + mixture A (80%–20%) (Bosch index) | 1.0 | 1.2 | 1.0 | 0.7 |

It must be observed that the comparisons have been made at the same power level. However, the heating power per liter of the mixture gas-oil+acetone-butanol mixture is slightly lower than that of the basic gas-oil, i.e. the gas-oil of the trade, when used alone.

The maximum powers observed have thus been:
50.2 HP (DIN) at 2000 r/min with basic gas-oil (50.2 HP DIN)
48.4 HP (DIN) at 2000 r/min with gas-oil+mixture A (80-20%) (48.4 HP DIN)
75.5 HP (DIN) at 4150 r/min with basic gas-oil (75.5 HP DIN)
73 HP (DIN) at 4150 r/min with gas-oil+mixture A (80-20%) (73 HP DIN)

This conforms with the respective heating powers per liter and with the slight yield increases observed, since the injection pumps are volumetric. A slight adjustment of the pump would permit recovery of the nominal power without disadvantage, when the yield increase is insufficient. But this adjustment is no longer necessary when adding to the above-mentioned motor fuels 5%, for example, of methanol (by weight). The effect of methanol is determined in example 9, as concerns tolerance to water.

EXAMPLE 8

The cetane number of various motor fuels whose composition is indicated in Table X, has been determined.

TABLE X

| Basic gas-oil of example 1 alone | Cetane number 54 |
|---|---|
| 90% gas-oil + 10% mixture A (defined in example 1) | Cetane number 49 |
| 80% gas-oil + 20% mixture A (defined in example 1) | Cetane number 41 |
| 70% gas-oil + 30% mixture A (defined in example 1) | Cetane number 36 |
| 50% gas-oil + 50% mixture A (defined in example 1) | Cetane number 30 |

It is possible to make use of a higher proportion of mixture A and to obtain a convenient cetane number, provided, however, that an additive is added to the obtained motor fuel, said additive consisting of:

(a) a small amount of oil (e.g. vegetal, inorganic or other oil) or any other additive convenient for obtaining the desired viscosity, (b) cetane number improvers, for example those of the alkyl nitrate type, etc . . . .

All the above indications are also applicable in the case of motor fuels containing methanol and also (a) gas-oil and (b) a mixture of butyl alcohol (n-butanol), acetone and isopropanol. The addition of methanol increases the cetane number in a proportion of about 0.35 point for each percent by weight of added methanol.

EXAMPLE 9

This example has the object of showing that, to the fuels or motor fuels of the invention, there can be added non negligible amounts of methanol which cannot be used alone. It is recalled that methanol cannot be added directly to gas-oil, in view of the spontaneous demixion phenomena which are enhanced by the presence of water, even in small amount. These mixtures of the acetone-butanol type may act as third solvents and thus provide for the possibility of adding methanol in amounts which depend on the nature and the percentages of the components which constitute the fuel or motor fuel.

Table XI below indicates the maximum percentages by weight of methanol in order to avoid the decrease in stability, the separation at cold and the separation at room temperature of different motor fuels containing (a) the gas-oil used in example 1 or a gas-oil US 2D containing 35% by weight of aromatic hydrocarbons and (b) the mixture A containing 75% by weight of butanol and 25% by weight of acetone or the mixture B containing by weight 70% of butanol, 15% of acetone and 15% of isopropanol.

TABLE XI

INFLUENCE OF THE ADDITION OF ABSOLUTE METHANOL (% by weight)

| COMPOSITION OF THE BASIC MIXTURE | STABILITY | COLD SEPARATION | SEPARATION AT ROOM TEMPERATURE |
|---|---|---|---|
| GAS-OIL OF EXAMPLE 1 | | | |
| Gas-oil 80% b. w. A 20% b. w. | 9.1 | 11.1 | 13.0 |
| Gas-oil 90% b. w. A 10% b. w. | 4.8 | 7.0 | 9.1 |
| Gas-oil 80% b. w. B 20% b. w. | 9.1 | 11.1 | 14.9 |
| Gas-oil 90% b. w. B 10% b. w. | 4.8 | 7.0 | 9.1 |
| GAS-OIL US 2 D (35% of AROMATICS) | | | |
| Gas-oil 80% b. w. A 20% b. w. | 14.9 | 16.7 | 20.0 |
| Gas-oil 90% b. w. A 10% b. w. | 7.0 | 9.1 | 11.1 |
| Gas-oil 80% b. w. B 20% b. w. | 11.1 | 13.0 | 18.4 |
| Gas-oil 90% b. w. B 10% b. w. | 7.0 | 9.1 | 11.1 |

EXAMPLE 10

Table XII below reports a few characteristics of motor fuels at low concentrations of butanol-acetone-ethanol mixture (by weight: 65% of butanol, 30% of acetone and 5% of ethanol).

TABLE XII

| Composition of the gasoline (by weight) | | | |
|---|---|---|---|
| % gasoline (with a 38% aromatic content) | 94 | 90 | 90 |
| % methanol | 4 | 6.5 | 8 |
| % butanol-acetone-ethanol mixture (M.B.A.E.) | 2 | 3.5 | 2 |
| Volumic mass at 20° C. (g/ml) | 0.756 | 0.757 | 0.757 |
| Reid vapor pressure (R.P.V.) (millibars) | 709 | 696 | 716 |
| Gums | 0 | 0 | 0 |
| Distillation | | | |
| Initial point | 36° C. | 38° C. | 36° C. |
| % distilled at 70° C. | 31% | 36% | 38% |
| % distilled at 100° C. | 51% | 53% | 54% |
| Final point | 196° C. | 193° C. | 191° C. |
| Research octane number | 99.5 | 100.0 | 100.6 |
| Motor octane number | 89.0 | 88.8 | 89.0 |

The tolerance to water is about 3 g per liter and generally increases on the one hand with the methanol/MBAE ratio and, on the other hand, with the percentage of aromatic hydrocarbons in the gasoline.

EXAMPLE 11

One liter of Jerusalem artichoke juice, obtained by pressing crushed tubers in a hydraulic press, is subjected to an acid hydrolysis by acidification at pH 2 with sulfuric acid while maintaining a temperature of 90° C. for 30 minutes, and then brought back to a pH of 6 by means of potassium hydroxide. A sterile addition of the following nutrients, contained in two liters of water, has been made: $(NH_4)_2SO_4$: 9 g; $K_2HPO_4$: 1.5 g; $MgSO_4$, 7 $H_2O$: 0.3 g; yeast extract: 0.75 g; $CaCO_3$: 4.5 g. The medium has been anaerobically sowed with 200 ml of a preculture of *Clostridium acetobutylicum* prepared on the same medium and the fermentation was allowed to proceed at 33° C. After 48 h, there was obtained, with a yield of 18% with respect to the sugars involved, a mixture containing 70% of butanol, 27% of acetone and 3% of ethanol.

EXAMPLE 12

A similar experiment was conducted but the stage of acid hydrolysis was replaced by sterilization for 20 minutes at 110° C. After culture of the same strain of Clostridium acetobutylicum, there was obtained, in three days, with a yield of 22% with respect to the sugars involved, a mixture containing 69% of butanol, 27% of acetone and 4% of ethanol.

EXAMPLE 13

Another test was conducted in which the juice was obtained by maceration of Jerusalem artichoke slices 1 mm thick (1 kg of Jerusalem artichoke for 2 liters of water). The pH was brought to 2.5 by addition of sulfuric acid and the maceration conducted for 45 minutes at 90° C. The obtained juice was neutralized at a pH of 6 with potassium hydroxide and the same nutrients as in example 1 were added to obtain the same final concentrations. The culture of *Clostridium acetobutylicum* was then conducted as precedingly and there was obtained in 48 hours a mixture of motor fuels containing 70% of butanol, 27% of acetone and 3% of ethanol, with a yield of 23% with respect to the sugars involved during 48 hours.

What is claimed is:

1. A blended high octane automotive fuel, comprising:
   (a) 90-96% by weight of a premium hydrocarbon gasoline;
   (b) 1-10% by weight of a mixture of butanol and acetone, 40-85% by weight of said mixture being butanol and 15-60% by weight being acetone; and
   (c) 3-10% by weight of methanol wherein the sum of (b) and (c) is at most 100%-(a).

2. A blended fuel according to claim 1, wherein said mixture (b) further comprises isopropanol.

3. A blended fuel according to claim 1, wherein in said mixture, the amount of butanol is 50-85% by weight; the amount of acetone is 15-25% by weight; and the amount of isopropanol is 5-35% by weight.

4. A blended fuel according to claim 1, wherein said mixture (b) further comprises ethanol.

5. A blended fuel according to claim 4, wherein in said mixture, the amount of butanol is 40-80% by weight; the amount of acetone is 15-45% by weight; and the amount of ethanol is 1-15% by weight.

6. A blended fuel according to claim 1, wherein said mixture further comprises isopropanol and ethanol, the amount of butanol in said mixture being 45-75% by weight; the amount of acetone being 15-25% by weight; the amount of isopropanol being 10-30% by weight; and the amount of ethanol being 1-10% by weight.

7. A blended fuel according to claim 1, wherein said mixture (b) is obtained by a process comprising the steps of:
(a) preparing cellulolytic enzymes by fermentation of an organism producing said enzymes;
(b) subsequently hydrolyzing a cellulosic substrate by contacting the substrate with the cellulolytic enzymes prepared in step (a), and recovering a sugar-containing hydrolysate; and
(c) effecting a fermentation of said hydrolysate, and recovering a mixture comprising butanol and acetone.

8. A blended fuel according to claim 7, wherein the organism used in step (a) is a bacterium belonging to the Clostridium genus, or a fungus belonging to the Sporotrichum, Polyporus, Penicillium, Fusarium, Myrothecium, or Trichoderma genera.

9. A blended fuel according to claim 7, wherein in step (c), an acetonobutylic fermentation of the hydrolysate is effected, in the presence of bacteria of the Clostridium genus selected from the species *Clostridium saccharoacetobutylicum, Clostridium acetobutylicum, Clostridium saccharobutyl acetonicum,* or *Clostridium saccharoperbutylicum.*

10. A blended fuel according to claim 7, wherein in step (c), a butanol/isopropanol fermentation of the hydrolysate is effected, in the presence of bacteria of the Clostridium genus selected from the species *Clostridium propylbutylicum, Clostridium Viscifasciens, Clostridium butylicum, Clostridium beijerinckii,* or *Clostridium toanum.*

11. A blended fuel according to claim 1, wherein said mixture (b) is obtained by a process comprising the steps of:
(a) hydrolyzing Jerusalem artichoke juice, and recovering a sugar-containing hydrolysate; and
(b) effecting a fermentation of said hydrolysate, and recovering a mixture comprising butanol and acetone.

12. An automotive fuel according to claim 1, comprising:
(a) about 94% by weight of said premium hydrocarbon gasoline;
(b) about 2% by weight of a mixture of 60% by weight butanol and 40% by weight acetone; and
(c) about 4% by weight of methanol.

13. An automotive fuel according to claim 1, comprising:
(a) about 94% by weight of sid premium hydrocarbon gasoline;
(b) about 2% by weight of a mixture of (i) 65% by weight of butanol, 30% by weight of acetone, and 5% by weight of ethanol, or (ii) 60% by weight of butanol, 30% by weight of acetone and 10% by weight of ethanol; and
(c) about 4% by weight of methanol.

14. A blended fuel, comprising:
(a) 75-90% by weight of gas-oil;
(b) 25-10% by weight of a mixture of butanol and acetone, 40-85% by weight of said mixture being butanol and 15-60% by weight being acetone; and
(c) 3-15% by weight of methanol wherein the sum of (b) and (c) is at most 100%-(a).

15. A blended fuel according to claim 14, comprising:
(a) about 76% by weight of gas-oil;
(b) about 19% by weight of a mixture of 75% by weight of butanol and 25% by weight of acetone; and
(c) about 5% by weight of methanol.

16. A blended fuel according to claim 14, wherein said mixture (b) further comprises isopropanol.

* * * * *